(12) United States Patent
Kojima (10) Patent No.: US 9,528,511 B2
(45) Date of Patent: Dec. 27, 2016

(54) LIQUID INJECTION DEVICE

(75) Inventor: Hideki Kojima, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 992 days.

(21) Appl. No.: 13/032,483

(22) Filed: Feb. 22, 2011

(65) Prior Publication Data

US 2011/0208224 A1    Aug. 25, 2011

(30) Foreign Application Priority Data

Feb. 22, 2010   (JP) ................. 2010-035780

(51) Int. Cl.
  *A61B 17/32*    (2006.01)
  *F04B 43/04*    (2006.01)
  *A61B 17/3203*  (2006.01)

(52) U.S. Cl.
  CPC ........... *F04B 43/04* (2013.01); *A61B 17/3203* (2013.01)

(58) Field of Classification Search
  CPC ............................ A61B 17/3203; F04B 43/04
  USPC ............ 604/65, 67, 118, 121, 151, 152, 246
  See application file for complete search history.

(56) References Cited

U.S. PATENT DOCUMENTS 8,287,485 B2 * 10/2012 Kimura et al. ................. 604/22
2008/0086077 A1   4/2008 Seto et al.
2009/0043480 A1   2/2009 Seto et al.
2010/0082054 A1 * 4/2010 Seto et al. ..................... 606/167
2010/0111708 A1 * 5/2010 Seto .................. A61B 17/3203
                                                       417/44.1
2011/0037795 A1 * 2/2011 Kojima .............. A61B 17/3203
                                                        347/10
2013/0218184 A1   8/2013 Seto et al.

FOREIGN PATENT DOCUMENTS

JP    2005-152127    6/2005
JP    2008-082202    4/2008
JP    2009-039384    2/2009

* cited by examiner

*Primary Examiner* — Gregory Anderson
*Assistant Examiner* — Sarah Simpson
(74) *Attorney, Agent, or Firm* — Workman Nydegger (57) ABSTRACT

A liquid injection device includes: a chamber to which the liquid to be injected is supplied and the injection nozzle is connected; a pump that pumps the liquid into the chamber; a volume varying unit that varies the volume of the chamber by being deformed according to a drive voltage applied thereto; and a drive voltage applying unit that applies the drive voltage having a predetermined voltage waveform to the volume varying unit in a state in which the liquid is supplied to the chamber, wherein the pump is a unit that pumps the liquid to the chamber in a state involving the pressure variations, and the drive voltage applying unit is a unit that applies the drive voltage to the volume varying unit while compensating the influence applied by the pressure variations of the pumped to the chamber on injection by varying the voltage waveform of the drive voltage.

6 Claims, 9 Drawing Sheets

FIG. 5A
PRESSURE AT PUMP OUTLET PORT

FIG. 5B
PRESSURE AT INLET PORT OF LIQUID CHAMBER

FIG. 5C
PRESSURE IN LIQUID CHAMBER

FIG. 6

FIG. 7A PRESSURE AT PUMP OUTLET PORT

FIG. 7B PRESSURE IN LIQUID CHAMBER

NO COMPENSATION BY DRIVE VOLTAGE WAVEFORM

FIG. 7C PRESSURE IN LIQUID CHAMBER

COMPENSATED BY DRIVE VOLTAGE WAVEFORM

LIQUID INJECTION DEVICE

This application claims priority to Japanese Patent Application No. 2010-035780, filed on Feb. 22, 2010, the entirety of which is hereby incorporated by reference.

BACKGROUND

1. Technical Field

The present invention relates to a technology for incising or excising living tissue by injecting pressurized liquid toward the living tissue.

2. Related Art

A technology for incising or excising tissue by pressurizing liquid such as water or physiologic saline and injecting the liquid from an injection nozzle toward the living tissue in a restricted state is developed (JP-A-2005-152127). This technology enables incision of tissue such as internal organ exclusively without damaging vascular structures such as blood vessels, and causes less damage to peripheral tissues. Therefore, burdens on patients can be reduced.

There is also proposed a technology configured to inject a pulsed jet stream intermittently when injecting liquid instead of injecting continuously from an injection nozzle, so that incision of the living tissue is enabled with a small amount of liquid injection (JP-A-2008-082202). In this technology, liquid to be injected is supplied to a small liquid chamber, and then pressurizing the liquid by reducing the volume of the liquid chamber instantaneously, thereby injecting liquid from the injection nozzle in a pulsed manner.

In order to inject the liquid from the injection nozzle, it is required to constantly supply the necessary and sufficient amount of liquid to the liquid chamber so that the liquid chamber is filled with the liquid. If air bubbles are entrained in the supplied liquid, even when the volume of the liquid chamber is reduced for injecting the liquid, the entrained air bubbles are crushed. Consequently, the liquid in the liquid chamber cannot be injected adequately by pressurizing liquid. Therefore, in the technology for injecting a pulsed jet stream, a volume variable pump which is capable of securing a sufficient flow rate without generating air bubbles is used as a pump for supplying the liquid in the liquid chamber instead of a centrifugal pump which is subject to generation of air bubbles.

However, since the liquid supply pressure is apt to vary when using the volume variable pump, there is a problem such that the operation of the liquid injection device is difficult. It is because the amount of liquid injected from the injection nozzle varies if the liquid supply pressure varies, and hence the incising capability varies or a reaction force that an operator feels when the liquid is injected varies. Therefore, in a technology for injecting liquid in a pulsed manner, it is obliged to use a specific pump which causes minimum pressure variations even though it is a volume variable type.

SUMMARY

An advantage of some aspects of the invention is to provide a technology which is capable of simplifying the operation of a liquid injection device even when the liquid varying in supplied pressure is supplied.

According to an aspect of the invention, there is provided a liquid injection device configured to inject liquid from an injection nozzle including: a liquid chamber to which the liquid to be injected is supplied and the injection nozzle is connected; a liquid pumping unit that pumps the liquid into the liquid chamber; a volume varying unit that varies the volume of the liquid chamber by being deformed according to a drive voltage applied thereto; and a drive voltage applying unit that applies the drive voltage having a predetermined voltage waveform to the volume varying unit in a state in which the liquid is supplied to the liquid chamber, wherein the liquid pumping unit is a unit that pumps the liquid to the liquid chamber in a state involving the pressure variations, and the drive voltage applying unit is a unit that applies the drive voltage to the volume varying unit while compensating the influence applied by the pressure variations of the liquid pumped to the liquid chamber on injection of the liquid by varying the voltage waveform of the drive voltage.

In this configuration, the liquid in the liquid chamber pressurized by pumping the liquid to the liquid chamber using the liquid pumping unit and reducing the volume of the liquid chamber by applying the drive voltage to the volume varying unit is injected from the injection nozzle. When applying the drive voltage to the volume varying unit, the influence of the pressure variations of the liquid pumped to the liquid chamber on injection of the liquid is compensated by varying the voltage waveform of the drive voltage.

Although detailed description will be given below, if the pressure of the liquid to be pumped to the liquid chamber varies, the force of the liquid to be injected from the injection nozzle varies. In contrast, the force of the liquid to be injected from the injection nozzle varies also by changing the voltage waveform of the drive voltage to be applied to the volume varying unit. Accordingly, by varying the voltage waveform of the drive voltage so as to cancel the influence of the pressure variations of the liquid to be pumped to the liquid chamber, the operation of the liquid injection device can be facilitated easily even when the pressure of the liquid to be pumped to the liquid chamber varies.

Preferably, the pressure of the liquid to be pumped to the liquid chamber is detected and, according to the detected pressure of the liquid, the drive voltage may be applied to the volume varying unit after having varied the voltage waveform thereof.

In this configuration, the voltage waveform of the drive voltage to be applied to the volume varying unit can be varied adequately according to the pressure of the liquid to be pumped to the liquid chamber. Consequently, the operation of the liquid injection device can be facilitated by the influence of the pressure variations of the liquid to be pumped to the liquid chamber.

Preferably, the voltage waveform is varied so as to increase the maximum potential difference of the drive voltage as the pressure of the liquid to be pumped to the liquid chamber is decreased, and then the drive voltage is applied to the volume varying unit.

Since the pressure of the liquid in the liquid chamber can be increased by varying the voltage waveform so that the maximum potential difference of the drive voltage is increased, the lowering of the pressure of the liquid to be pumped into the liquid chamber can be compensated. Consequently, the operation of the liquid injection device can be facilitated even when the pressure of the liquid to be pumped to the liquid chamber is lowered.

When the pressure of the liquid to be pumped to the liquid chamber is increased, the drive voltage may be applied to the volume varying unit after having varied the voltage waveform so that the maximum potential difference of the drive voltage is decreased with increase in pressure. Accordingly, since the pressure increase in the liquid chamber due to the volume variations in the liquid chamber can be restrained, the increase in pressure of the liquid to be pumped into the liquid chamber can be compensated. Consequently, the operation of the liquid injection device can be facilitated even when the pressure of the liquid to be pumped to the liquid chamber is increased.

Preferably, in the liquid injection device, the voltage waveform is varied so as to increase the speed of voltage rising of the drive voltage as the pressure of the liquid to be pumped to the liquid chamber is decreased, and then applied to the volume varying unit.

Since the pressure of the liquid in the liquid chamber can be increased by varying the voltage waveform so that the voltage rising speed of the drive voltage is increased, the lowering of the pressure of the liquid to be pumped into the liquid chamber can be compensated. Consequently, the operation of the liquid injection device can be facilitated even when the pressure of the liquid to be pumped to the liquid chamber is lowered.

When the pressure of the liquid to be pumped to the liquid chamber is increased, the drive voltage may be applied to the volume varying unit by varying the voltage waveform so that the voltage rising speed of the drive voltage is lowered with increase in pressure. Accordingly, since the pressure increase in the liquid chamber due to the volume variations in the liquid chamber can be restrained, the increase in pressure of the liquid to be pumped to the liquid chamber can be compensated. Consequently, even when the pressure of the liquid to be pumped to the liquid chamber rises, the operation of the liquid injection apparatus can be facilitated.

BRIEF DESCRIPTION OF THE DRAWINGS

The invention will be described with reference to the accompanying drawings wherein like numbers reference like elements.

DESCRIPTION OF EXEMPLARY EMBODIMENTS

Figure 1:
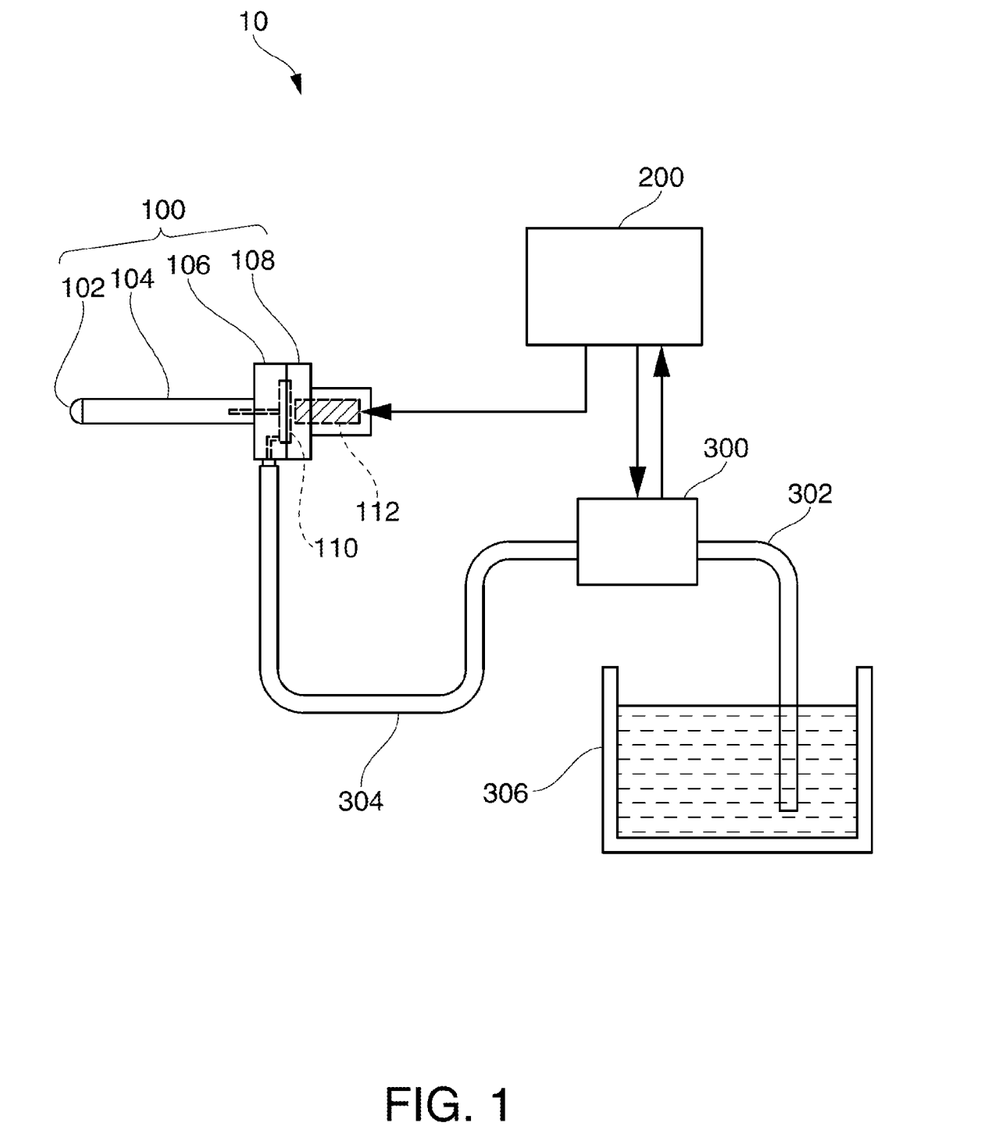
FIG. 1 is an explanatory drawing showing a rough configuration of a liquid injection device according to a first embodiment.

In the following description, in order to clarify contents of the invention, embodiments will be described in the following order.
A. First Embodiment
 A-1. Configuration of Device
 A-2. Liquid Injecting Action
 A-3. Method of Driving Actuator
 A-4. Modification of First Embodiment
B. Second Embodiment
A. First Embodiment
A-1. Configuration of Device FIG. 1 is an explanatory drawing showing a rough configuration of a liquid injection device 10 according to a first embodiment. The illustrated liquid injection device 10 according to the first embodiment roughly includes an injection unit 100 configured to inject liquid in a pulsed manner, a supply pump 300 configured to supply liquid to be injected from the injection unit 100 toward the injection unit 100, and a control unit 200 configured to control actions of the injection unit 100 and the supply pump 300.

The injection unit 100 has a configuration including a substantially rectangular front block 106 formed of metal and a rear block 108, which is also formed of metal, placed on the rear side of the front block 106 and secured thereto with a screw, and a circular tube shaped liquid channel tube 104 is provided on the front surface of the front block 106 so as to extend upright therefrom, and an injection nozzle 102 is inserted to a distal end of the liquid channel tube 104. Provided on a mating plane between the front block 106 and the rear block 108 is a thin disk-shaped liquid chamber 110. The liquid chamber 110 is connected to the injection nozzle 102 via the liquid channel tube 104. Provided inside the rear block 108 is an actuator 112 formed of a laminated piezoelectric element. The volume of the liquid chamber 110 can be varied by deforming the liquid chamber 110 by driving the actuator 112.

The supply pump 300 is configured to suck liquid to be injected (water, physiologic saline, drug solution, etc.) from a liquid tank 306 having the liquid stored therein via a tube 302, and then supply the liquid into the liquid chamber 110 of the injection unit 100 via a tube 304. The supply pump 300 is required to be capable of supplying a necessary and sufficient amount of liquid according to a request of the injection unit 100, and not to allow air bubbles to be trapped in the liquid. Therefore, a volume variable pump (piston pump, diaphragm pump, etc.) configured to pump liquid by sucking liquid into the liquid chamber 106 which can be increased and decreased in volume and then reducing the volume of the liquid chamber is used instead of a centrifugal pump which pumps liquid by rotating a wind-mill shaped member (so-called vane or impeller) within a case.

The supply pump 300 used in the liquid injection device 10 in the first embodiment is assumed to be the piston pump which pumps the liquid in the liquid chamber by sliding two pitons in cylinders. The two pistons are configured to slide in phases opposite from each other such that one piston moves forward while the other piston moves backward. Therefore, the liquid can be pumped toward the injection unit 100 without interruption. As a matter of course, the pressure for pumping the liquid cannot be uniformized only by causing the two pistons to slide in the opposite phases. Therefore, the liquid is supplied to the injection unit 100 with pressure variations.

The control unit 200 controls an action of the liquid injection device 10 by controlling the actuator 112 built in the injection unit 100 or the supply pump 300. As described above, in the liquid injection device 10 in the first embodiment, the liquid with pressure variations is supplied from the supply pump 300 to the injection unit 100. Accordingly, a phase signal is supplied from the supply pump 300 to the control unit 200. The phase signal is a signal output every time one of the pistons sliding in the supply pump 300 passes through a predetermined position. The pressure variations of the liquid supplied to the injection unit 100 is generated by a reciprocal motion of the pistons. Therefore, the phase of the pressure variations of the liquid supplied to the injection unit 100 can be found on the basis of the phase signal output every time the piston passes through the predetermined position. Although detailed description will be given below, in the liquid injection device 10 of the first embodiment, since the drive mode of the actuator 112 integrated in the injection unit 100 is varied on the basis of the phase signal, the operation of the liquid injection device 10 is facilitated even when the pressure variations are included in the liquid supplied to the injection unit 100.

Figure 2A:
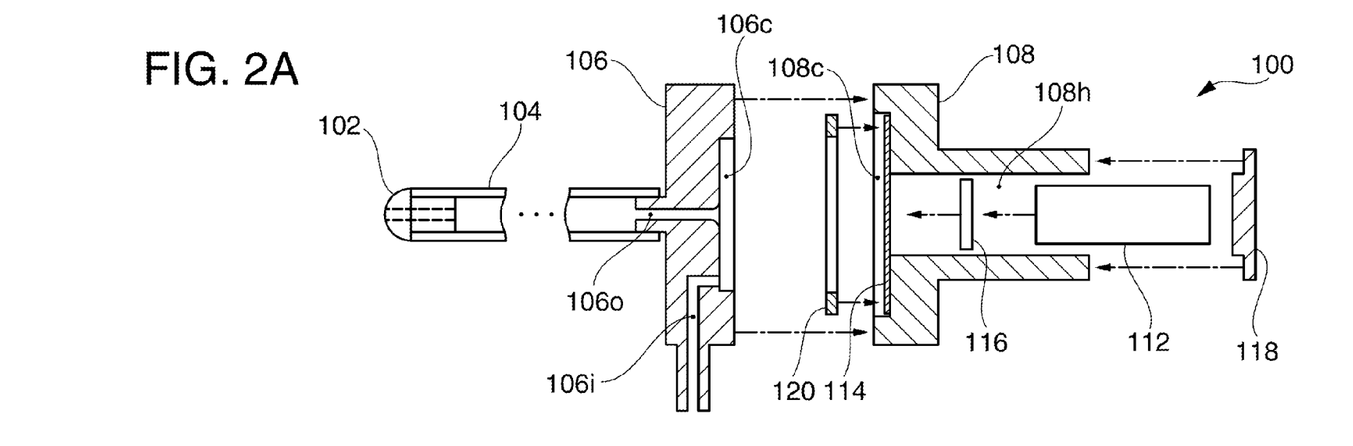
FIGS. 2A and 2B are explanatory drawings showing a detailed structure of an injection unit.
Figure 2B:
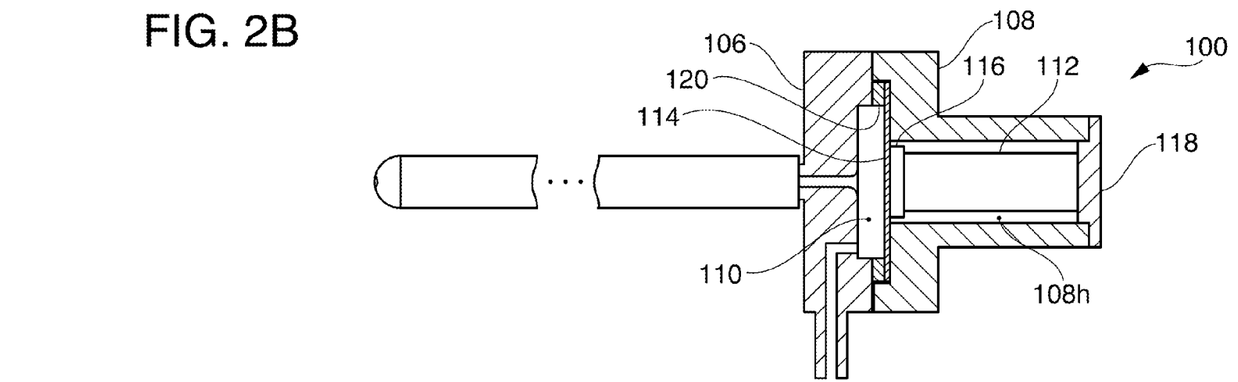

FIGS. 2A and 2B are explanatory drawings showing a detailed structure of the injection unit 100. FIG. 2A is an exploded cross-sectional view of the injection unit 100, and FIG. 2B is a cross-sectional view after assembly. The rear block 108 is formed with a large circular and shallow depression 108c at a substantially center of the mating surface with respect to the front block 106. The depression 108c is formed with a through hole 108h having a circular cross section at a center position thereof so as to penetrate through the rear block 108.

Provided on a bottom portion of the depression 108c is a metallic thin diaphragm 114 so as to close the through hole 108h. In addition, a peripheral edge portion of the diaphragm 114 is secured to the bottom portion of the depression 108c in an air-tight manner by a method such as brazing or diffusion bonding. An annular shaped metallic reinforcing plate 120 is loosely fitted to the depression 108c from above the diaphragm 114. The thickness of the reinforcing plate 120 is set to a thickness so that an end surface of the rear block 108 formed with the depression 108c and an end surface of the reinforcing plate 120 are flush with each other when the reinforcing plate 120 is fitted from above the diaphragm 114.

The through hole 108h closed by the diaphragm 114 accommodates the actuator 112 (a laminated piezoelectric element in the first embodiment), and on the rear side of the actuator 112, the through hole 108h is closed by a disk-shaped metallic bottom plate 118. A circular metallic shim 116 is accommodated between the actuator 112 and the diaphragm 114. The thickness of the shim 116 is selected so that the diaphragm 114, the shim 116, the actuator 112, and the bottom plate 118 come in contact with each other when the actuator 112 is accommodated in the through hole 108h of the rear block 108 and the through hole 108h is closed with the bottom plate 118.

The front block 106 is formed with a circular and shallow depression 106c on the mating surface with respect to the rear block 108. The inner diameter of the depression 106c is set to be almost the same as the inner diameter of the reinforcing plate 120 fitted to the rear block 108. When the front block 106 and the rear block 108 are mated and secured with each other with the screw, the inner peripheral surfaces of the diaphragm 114 and the reinforcing plate 120 provided on the side of the rear block 108 and the depression 106c provided on the front block 106 define substantially the disk-shaped liquid chamber 110.

The front block 106 is provided with a supplying channel 106i for supplying liquid to the liquid chamber 110 from the side of the front block 106. In addition, a small-diameter injection channel 106o which allows passage of liquid pressurized in the liquid chamber 110 is penetrated through the depression 106c at the center position thereof. An inner diameter portion of the liquid channel tube 104 is fitted on a portion where the injection channel 106o opens. Then, the injection nozzle 102 is fitted on a distal end of the liquid channel tube 104. Therefore, the cross-sectional area of the channel of the liquid injected from the liquid chamber 110 is configured to be increased in the liquid channel tube 104 after the injection channel 106o, and then is decreased again in a portion of the injection nozzle 102 at the distal end of the liquid channel tube 104.

FIG. 2B is a cross-sectional view showing a state in which the injection unit 100 is assembled. As illustrated in the drawing, the end surface of the reinforcing plate 120 is flush with the end surface of the rear block 108, and the liquid chamber 110 is defined between the front block 106 and the rear block 108 when mating the front block 106 to this surface. When the shim 116 and the actuator 112 are accommodated in the through hole 108h of the rear block 108 and the bottom plate 118 is mounted, the diaphragm 114, the shim 116, the actuator 112, and the bottom plate 118 come into just contact with each other.

A-2. Liquid Injecting Action

Figure 3A:
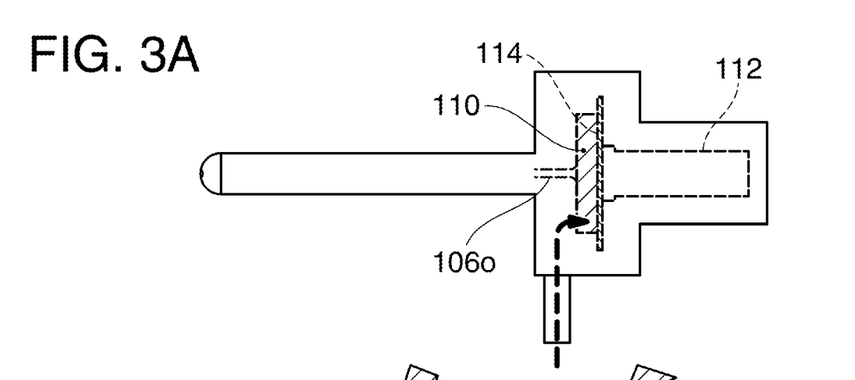
FIGS. 3A and 3B are explanatory drawings showing an action of the injection unit injecting liquid according to the first embodiment.
Figure 3B:
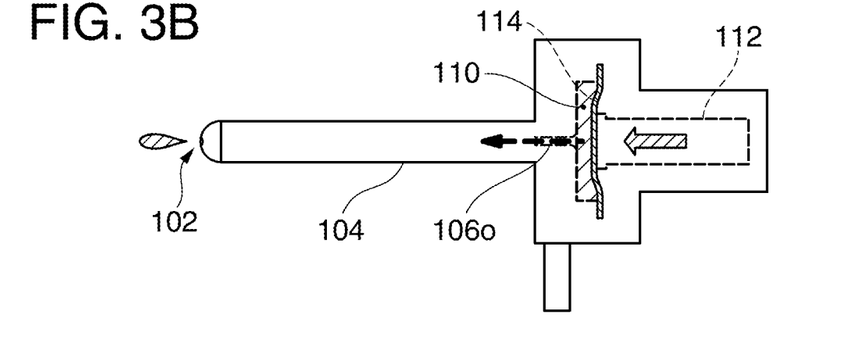

FIGS. 3A and 3B are explanatory drawings showing an action of the injection unit 100 injecting liquid according to the first embodiment. FIG. 3A illustrates a state in which the supply pump 300 is driven but the actuator 112 is not driven (a state before application of the drive voltage). In this state, as indicated by a thick broken arrow in the drawing, the liquid chamber 110 is filled with liquid supplied by the supply pump 300. The drawing indicates that the liquid chamber 110 is filled with the liquid by hatching the liquid chamber 110.

Subsequently, the actuator 112 is driven by applying the drive voltage. Then, the actuator 112 is deformed in the direction of elongation, thereby making an attempt to deform the diaphragm 114 and reduce the volume of the liquid chamber 110. Consequently, the liquid in the liquid chamber 110 is pressurized, and is injected from the injection nozzle 102 via the injection channel 106o and the liquid channel tube 104. The cubic measure of the liquid injected at this time is almost equal to the volume of the liquid chamber 110 reduced by the deformation of the actuator 112.

In addition to the injection channel 106o, the supplying channel 106i is also connected to the liquid chamber 110. Therefore, the liquid pressurized in the liquid chamber 110 is considered to flow out not only from the injection channel 106o, but also from the supplying channel 106i. However, actually, the liquid pressurized in the liquid chamber 110 flows out exclusively from the injection channel 106o, and does not flow out from the supplying channel 106i. The reason will be described below. First of all, since the liquid in the supplying channel 106i attempts to flow into the liquid chamber 110, the flow of the liquid in the supplying channel 106i needs to be pushed backward in order to allow the liquid pressurized in the liquid chamber 110 to flow out from the supplying channel 106i. In addition, since the liquid in the supplying channel 106i is pumped by the supply pump 300 from behind, the pressurized liquid must overcome the pressure of the pump as well. In contrast, in the injection channel 106o, there is no flow of liquid which hinders an outflow from the liquid chamber 110, and the pressure of the supply pump 300 for pumping the liquid does not act in the direction which hinders the outflow from the liquid chamber 110. Therefore, the liquid pressurized in the liquid chamber 110 flows out not from the supplying channel 106i, but exclusively from the injection channel 106o. In addition, by adjusting the cross-sectional areas and the lengths of the injection channel 106o and the supplying channel 106i, the inertance of the supplying channel 106i is increased to a level larger than that of the injection channel 106o so as to act in the direction which allows easy outflow of the liquid pressurized in the liquid chamber 110 from the injection channel 106o. For example, the inertance of the supplying channel 106i can be set to a level larger than that of the injection channel 106o by setting the cross-sectional area of the liquid channel at a portion immediately out of the front block 106 (that is, the cross-sectional area of the liquid channel tube 104) to be larger than the cross-sectional area of the supplying channel 106i or by shortening the length of the injection channel 106o to be shorter than that of the supplying channel 106i. From these reasons, the liquid pressurized in the liquid chamber 110 flows out exclusively from the injection channel 106o, and does not flow out from the supplying channel 106i.

FIG. 3B illustrates a state in which the drive voltage is applied to the actuator 112, and hence the actuator 112 is deformed to reduce the volume of the liquid chamber 110, whereby the liquid is injected from the injection nozzle 102 in a pulsed manner by an amount pushed out from the liquid chamber 110.

When the pulsed liquid is injected in this manner, the voltage applied to the actuator 112 is removed. Then, the deformed actuator 112 is restored to the original length and the volume of the liquid chamber 110 reduced correspondingly is restored to the original volume. With this movement, the liquid is supplied from the supply pump 300 to the liquid chamber 110 and, consequently, the actuator 112 shown in FIG. 3A is restored to the state before driving the actuator 112. When the drive voltage is applied to the actuator 112 again from this state, and hence the actuator 112 is deformed as shown in FIG. 3B, whereby the liquid is injected from the injection nozzle 102 in a pulsed manner by an amount pushed out from the liquid chamber 110. In this manner, in the liquid injection device 10 in the first embodiment, every time the drive voltage is applied to the actuator 112, the pulsed liquid can be injected from the injection nozzle 102.

Figure 4:
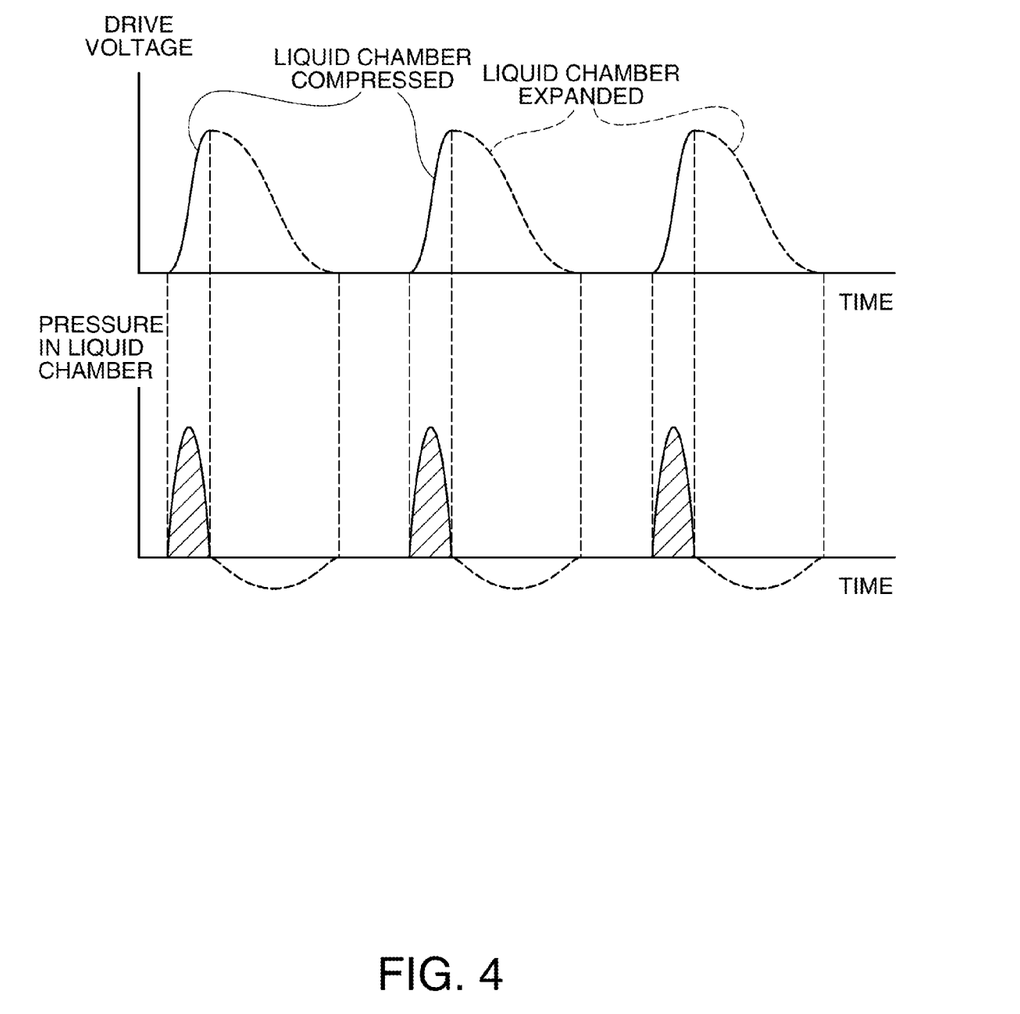
FIG. 4 is an explanatory drawing conceptually showing a state in which the liquid in the liquid chamber is pressurized by an application of a drive voltage to an actuator.

FIG. 4 is an explanatory drawing conceptually showing a state in which the liquid in the liquid chamber 110 is pressurized by an application of the drive voltage to the actuator 112. Since FIG. 4 shows only a pressure raised or lowered by the actuator 112, the pressure when the liquid is supplied from the supply pump 300 to the liquid chamber 110 is not included. On the upper level of the drawing, a drive voltage waveform to be applied to the actuator 112 is shown. On the lower level of the drawing, a state in which the pressure in the liquid chamber 110 varies by the deformation of the liquid chamber 110 caused by the actuator 112 is conceptually shown. In the first embodiment, when the voltage to be applied to the actuator 112 is raised, the actuator 112 is deformed in the expanding direction and hence the volume of the liquid chamber 110 is reduced. In contrast, when the voltage to be applied is lowered, the volume of the liquid chamber 110 is increased.

In the drive voltage waveform shown in FIG. 4, the liquid chamber 110 is compressed at portions indicated by solid lines, and the liquid chamber 110 is enlarged at portions indicated by broken lines. At the portions where the liquid chamber 110 is compressed (portions where the drive voltage waveforms are indicated by solid lines), the liquid in the liquid chamber 110 is compressed and, consequently, the liquid is injected from the injection nozzle 102. Subsequently, at the portions where the volume of the liquid chamber 110 is restored (portions where the drive voltage waveform are indicated by broken lines), the pressure of the liquid chamber 110 is lowered and, consequently, the liquid is supplied from the supplying channel 106i into the liquid chamber 110. Here, when the pressure of the liquid supplied from the supply pump 300 is varied, the following state is generated.

Figure 5A:
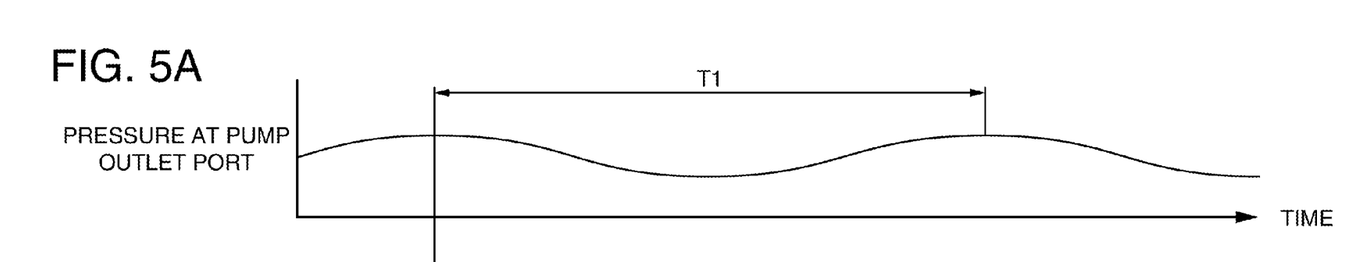
FIGS. 5A to 5C are explanatory drawings conceptually showing a phenomenon occurring when the liquid including pressure variations is supplied from a supply pump.
Figure 5B:
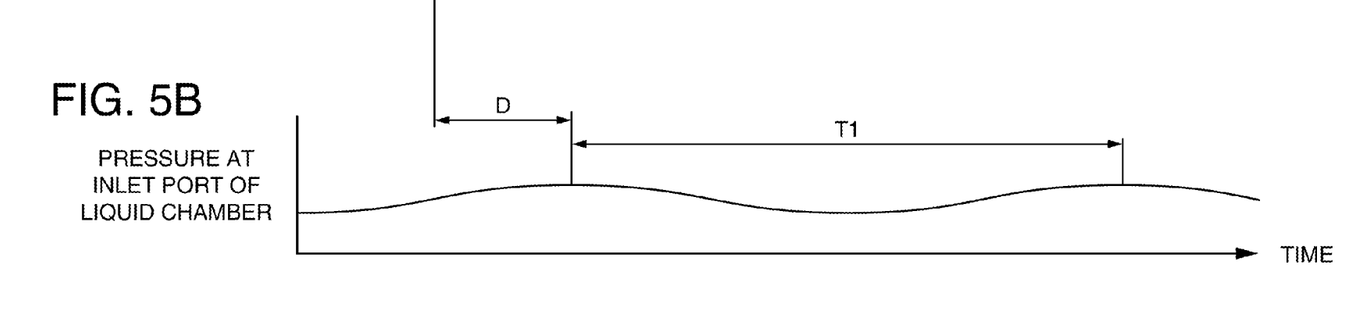
Figure 5C:
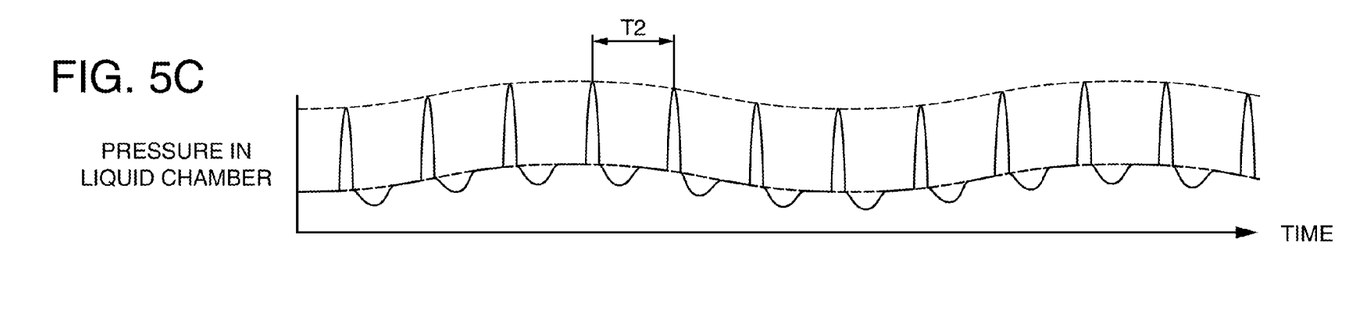

FIGS. 5A to 5C are explanatory drawings conceptually showing a phenomenon occurring when the pressure variations are involved in the liquid that the supply pump 300 supplies toward the injection unit 100. For example, it is assumed that the liquid pressure at the outlet portion of the supply pump 300 is varied at a period T1 as shown in FIG. 5A. The pressure variations involves a slight time delay D at a portion of the tube 304 which connects the supply pump 300 and the injection unit 100 and also includes a slight reduction of the pressure amplitude. Consequently, the liquid is supplied to the liquid chamber 110 of the injection unit 100 in a state in which the pressure is varied as shown in FIG. 5B. Therefore, in a state in which the actuator 112 is not driven, the pressure in the liquid chamber 110 is varied in a state shown in FIG. 5B.

From this state, the actuator 112 is driven using the drive voltage waveform shown in FIG. 4. Then, the pressure in the liquid chamber 110 is increased or reduced according to the movement of the liquid chamber 110 being compressed or expanded by the actuator 112. Consequently, when the drive voltage waveform at a period T2 is applied to the actuator 112, for example, the pressure in the liquid chamber 110 is varied in a state in which a short-period variation varied at the period T2 is superimposed on a long-period variation varied at the period T1 as shown in FIG. 5C.

When the pressure in the liquid chamber 110 is varied in a state shown in FIG. 5C, the operation of the liquid injection device 10 becomes difficult as shown below. First of all, the liquid is injected from the injection nozzle 102 at an interval of the period T2 in a pulsed manner, and the force of injection of the liquid varies from one pulse to another. Therefore, the incising capability of the living tissue varies as well and, consequently, such event that the tissue is excessively cut or, in contrast, is not cut enough may occur. Since the pressure in the outside of the injection nozzle 102 is constantly at atmospheric pressure, when the pressure in the liquid chamber 110 varies, the flow rate of the liquid injected from the injection nozzle 102 correspondingly is varied. The variations in injected flow rate also cause variations in incising capability.

In addition, when the liquid is injected from the injection nozzle 102, the reaction force is transmitted to the injection unit 100. Therefore, when the force of the liquid injected from the injection nozzle 102 varies, a force required for retaining the injection unit 100 also varies and, consequently, an operator of the liquid injection device 10 can hardly retain the injection unit 100 at the same position. From the reasons as described above, the operation of the liquid injection device 10 becomes difficult when the pumping pressure of the supply pump 300 varies. Therefore, in the liquid injection device 10 in the first embodiment, even when the pressure variations exist in the liquid from the supply pump 300, the operation of the liquid injection device 10 is facilitated by varying the drive voltage waveform applied to the actuator 112 according to the pressure of the liquid supplied from the supply pump 300.

A-3. Method of Driving Actuator

Figure 6:
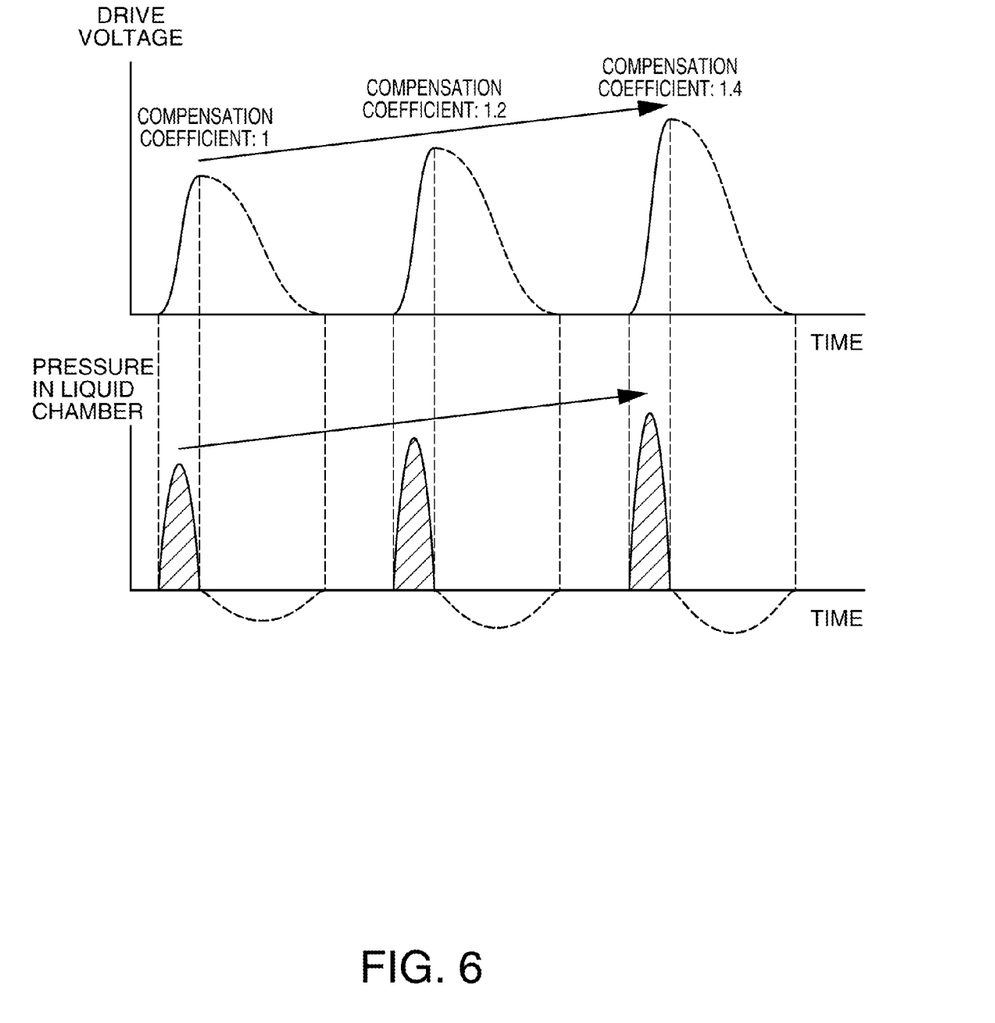
FIG. 6 is an explanatory drawing showing a state in which a drive voltage waveform that the liquid injection device according to the first embodiment applies to the actuator.

FIG. 6 is an explanatory drawing showing a state in which the drive voltage waveform that the liquid injection device 10 in the first embodiment applies to the actuator 112 is changed. In the first embodiment, the drive voltage waveform stored as a standard is multiplied by a compensation coefficient, so that the drive voltage waveform to be applied to the actuator 112 is changed. For example, the drive voltage waveform shown at the left end from among the drive voltage waveforms shown on the upper level in FIG. 6 is a waveform multiplied by a compensation coefficient "1" (that is, the standard drive voltage waveform), the drive voltage waveform shown at the center is a waveform multiplied by a compensation coefficient "1.2", and the drive voltage waveform shown at the right end is a waveform multiplied by a compensation coefficient "1.4".

On the lower portion of FIG. 6, a state in which the pressure in the liquid chamber 110 varies according to the respective drive voltage waveforms is shown. As illustrated, the larger the compensation coefficient (the higher the maximum voltage of the drive voltage waveform), the larger a peak value of the pressure generated in the liquid chamber 110 becomes. In contrast, the smaller the compensation coefficient, the smaller the peak value of the pressure generated in the liquid chamber 110 becomes. Therefore, in the liquid injection device 10 in the first embodiment, the difficulty of the operation of the liquid injection device 10 caused by the pressure variations of the liquid from the supply pump 300 is cleared by multiplying the drive voltage waveform to be applied to the actuator 112 by the compensation coefficient as described above.

Figure 7A:
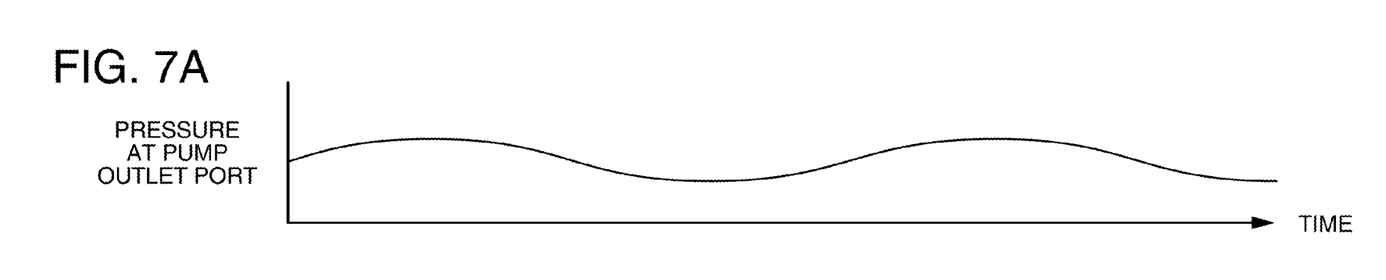
FIGS. 7A to 7C are explanatory drawings showing a state in which difficulty of operation of the liquid injection device according to the first embodiment caused by the pressure variations of supplied liquid is cleared by multiplying the drive voltage waveform by a compensation coefficient.
Figure 7B:
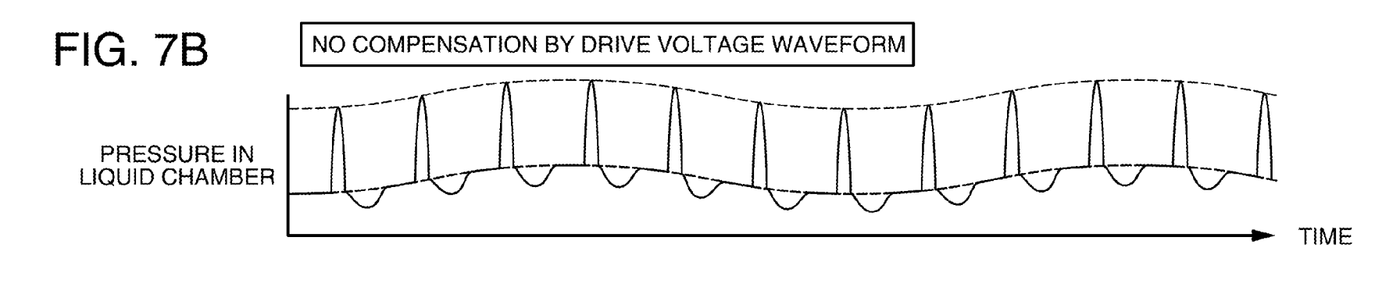
Figure 7C:
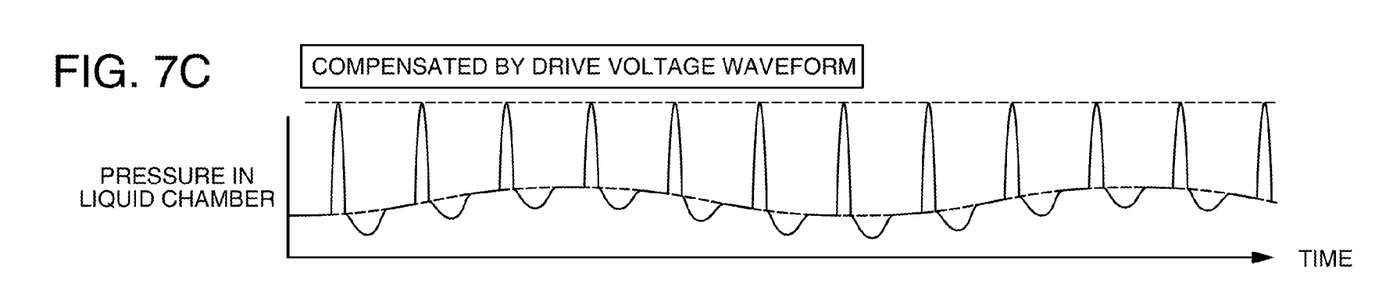

FIGS. 7A to 7C are explanatory drawings showing a state in which the difficulty of operation of the liquid injection device 10 according to the first embodiment caused by the variations in liquid supply pressure from the supply pump 300 is cleared by multiplying the drive voltage waveform by the compensation coefficient. For example, if the pressure applied when the supply pump 300 pumps the liquid varies as shown in FIG. 7A, and the actuator 112 is driven using the standard (not multiplied by the compensation coefficient) drive voltage waveform, the pressure in the liquid chamber 110 varies as shown in FIG. 7B. Consequently, as described above in conjunction with FIGS. 5A to 5C, the operation of the liquid injection device 10 can be facilitated.

Therefore, at the portions where the pressure of the liquid to be supplied to the liquid chamber 110 is lowered, the peak values of the pressure in the liquid chamber 110 become substantially the same value as shown in FIG. 7C by applying the voltage to the actuator 112 after having multiplied the drive voltage waveform by a compensation coefficient larger than "1". As described above in conjunction with FIGS. 5A to 5C, the pressure variations of the liquid to be supplied to the liquid chamber 110 includes the phase delay or the amplitude attenuation in contrast to the pressure variations of the liquid pumped by the supply pump 300. However, such delay or attenuation can be found in advance because these values are almost determined by the length or the rigidity of the tube 304 which connects the supply pump 300 and the injection unit 100. How the pressure of the liquid pumped by the supply pump 300 is varied after the phase signal is output from the supply pump 300 can be found out in advance. Therefore, by setting the adequate compensation coefficients in advance according to the time elapsed from the time point of reception of the phase signal, the peak values of the pressure in the liquid chamber 110 can be aligned to substantially the same value as shown in FIG. 7C.

In FIG. 5, although the magnitude of the time delay D generated in the tube 304 is displayed with exaggeration, the time delay D does not have to be large. Therefore, to be more simple, the compensation coefficient may be set by ignoring the influence of the time delay D and considering only the attenuation of the pressure variations by the tube 304. In FIG. 7C, it is assumed that the liquid is injected in a pulsed manner at a constant cycle. However, as is clear from the description given above, the peak values at every pulse can be aligned to the substantially same pressure even when the liquid is injected at an arbitrary timing instead of the case where the liquid is injected at the constant cycle.

By setting the force of the liquid injected from the injection nozzle 102 to be substantially constant by multiplying the drive voltage waveform by the compensation coefficient in this manner, the incising capability of the liquid injection device 10 can be maintained to be substantially constant. The flow rate of the liquid injected by every pulse can also be maintained to be substantially constant. In addition, the reaction force that the injection unit 100 receives when the liquid is injected from the injection nozzle 102 can be maintained substantially constant. Therefore, even when the pressure of the liquid pumped from the supply pump 300 varies, the operation of the liquid injection device 10 can be facilitated.

The waveform of this embodiment is only an example, and may be modified such as a squire wave and a rectangular wave without departing from the scope of the invention.

A-4. Modification of First Embodiment

In the first embodiment described above, the description is made on the assumption that the influence of the pressure variations from the supply pump 300 is compensated by multiplying the drive voltage waveform to be applied to the actuator 112 by the compensation coefficient and deforming (that is, enlarging or contracting) the drive voltage waveform while maintaining the analogous shape thereof. However, the influence of the pressure variations from the supply pump 300 may be compensated by deforming the drive voltage waveform into a non-analogous shape.

A modification of the first embodiment described above will be described below.

In the modification of the first embodiment, the drive voltage waveform to be applied to the actuator 112 is stored by dividing into portions in which the voltage value is increased (the voltage rise portion), and portions in which the voltage value is decreased (the voltage dropped portion). By changing the time required for outputting the voltage rise portion, the drive voltage waveform to be applied to the actuator 112 is deformed. For example, when it is assumed that the drive voltage waveform stored as a standard is a voltage waveform in which the voltage rise portion is output using a period ta and then the voltage dropped portion is output using a period tb, the drive voltage waveform is deformed by shortening or elongating the period required for outputting the voltage rise portion. It is also possible to change the period tb of the voltage dropped portion simultaneously with a change of the period ta of the voltage rise portion.

Figure 8:
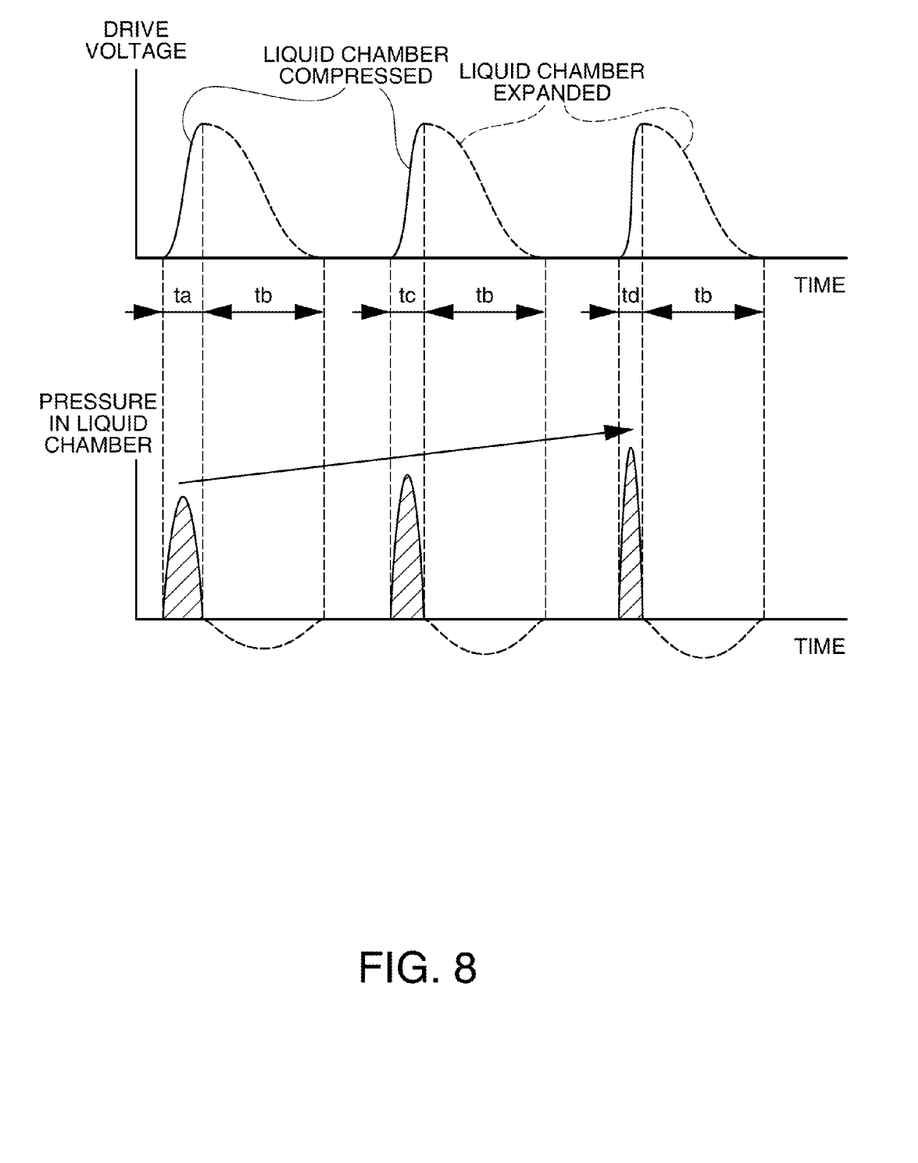
FIG. 8 is an explanatory drawing showing a state in which a drive voltage waveform is deformed by the liquid injection device according to a modification of the first embodiment.

FIG. 8 is an explanatory drawing showing a state in which a drive voltage waveform is modified by the liquid injection device 10 according to a modification of the first embodiment. The voltage waveform shown at the left end from among the three drive voltage waveforms shown on the upper level in FIG. 8 is a drive voltage waveform stored as a standard. The drive voltage waveform shown at the center is a voltage waveform in which the period required for outputting a voltage rise portion is shortened from the standard period ta to a period tc (=0.8×ta). In addition, the drive voltage waveform shown at the right end is a voltage waveform in which the period of the voltage rise portion is shortened to a period td (=0.6×ta).

The voltage value applied to the actuator 112 rises abruptly as the period required for outputting the voltage rise portion is shortened in this manner. Therefore, the actuator 112 is deformed abruptly to reduce the volume of the liquid chamber 110 abruptly. Consequently, the peak value of the pressure applied to the liquid in the liquid chamber 110 is increased. On the lower level in FIG. 8, a state in which the peak value of the pressure in the liquid chamber 110 is increased as the period of the voltage rise portion of the drive voltage waveform is shortened is shown. In FIG. 8, only a case where the period required for outputting the voltage rise portion is shortened is illustrated. However, when the period required for outputting the voltage rise portion is elongated, the peak value of the pressure in the liquid chamber 110 is reduced. Therefore, the drive voltage waveform is deformed by multiplying the drive voltage waveform by the compensation coefficient determined on the basis of the phase signal from the supply pump 300 as a reference in the liquid injection device 10 of the first embodiment described above. In contrast, in the liquid injection device 10 in the modification in the first embodiment, the operation can be facilitated in the same manner also by deforming the drive voltage waveform by shortening (or elongating) the period required for outputting the voltage rise portions with reference to the phase signal because the influence of the pressure variations of the liquid supplied from the supply pump 300 is cancelled.

The waveform of this embodiment is only an example, and may be modified such as the rectangular wave and a saw tooth wave without departing from the scope of the invention.

B. Second Embodiment

In the liquid injection device 10 in the first embodiment described above, the description is made on the assumption that the drive voltage waveform is deformed on the basis of the phase signal from the supply pump 300, and then the deformed drive voltage waveform is applied to the actuator 112. However, the influence of the pressure variations may be compensated by deforming the drive voltage waveform according to the detected pressure by detecting the pressure variations of the liquid supplied to the liquid chamber 110 instead of receiving the phase signal from the supply pump 300.

Figure 9:
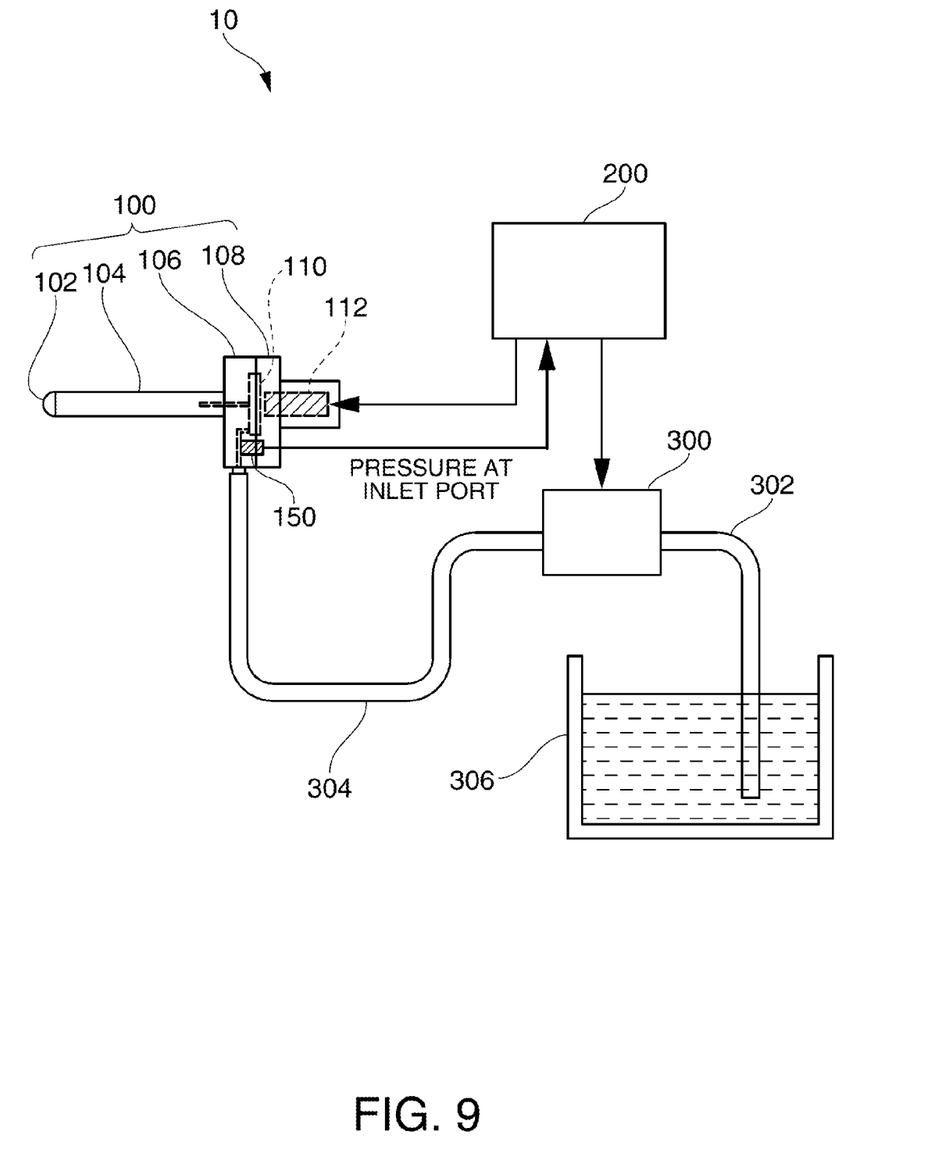
FIG. 9 is an explanatory drawing showing a rough configuration of the liquid injection device according to a second embodiment.

FIG. 9 is an explanatory drawing showing a rough configuration of the liquid injection device 10 according to a second embodiment. Description of the same configurations as the liquid injection device 10 in the first embodiment described above from among the configurations of the liquid injection device 10 in the second embodiment by assigning the same numerals will be omitted.

As shown in FIG. 9, in the liquid injection device 10 in the second embodiment, the phase signal is not output from the supply pump 300 toward the control unit 200. Instead, a pressure sensor 150 is provided in the injection unit 100 so that the pressure of the liquid supplied from the supply pump 300 can be detected in the vicinity of an inlet port of the liquid chamber 110. When the detected pressure is lower than the standard pressure, the drive voltage waveform of the actuator 112 is multiplied by a compensation coefficient larger than "1" (or shortening the period required for the voltage rise portions). In contrast, when the detected pressure is higher than the standard pressure, the drive voltage waveform is multiplied by a compensation coefficient smaller than "1" (or elongating the period required for the voltage rise portions). Accordingly, since the influence of the pressure variations of the liquid supplied from the supply pump 300 is cancelled by multiplying the drive voltage waveform by a compensation coefficient of an adequate value or by reducing (or elongating) the period required for the voltage rise portion at an adequate ratio according to the detected voltage of the liquid, the operation can be facilitated.

In the liquid injection device 10 according to the second embodiment described above, the influence of the pressure variations of the liquid pumped into the liquid chamber is cancelled by the deformation of the drive voltage waveform according to the detected pressure even when the pressure of the liquid to be supplied to the liquid chamber 110 is varied irregularly from some reasons, so that the operation of the liquid injection device 10 can be facilitated.

Although the liquid injection device in various embodiments has been descried, the invention is not limited to all of the embodiments and the modifications described above, and various modes may be implemented without departing the scope of the invention.

What is claimed is:

1. A liquid injection device configured to inject liquid from an injection nozzle comprising:
   a liquid supplying unit configured to supply liquid to a liquid chamber connected to the injection nozzle;
   a volume varying unit configured to vary a volume of the liquid chamber according to a drive voltage applied to the volume varying unit; and
   a controller configured to apply the drive voltage to the volume varying unit, wherein the drive voltage has a voltage waveform,
   wherein the liquid supplying unit is configured to output a phase signal to the controller, the phase signal indicates a pressure variation of the liquid supplied from the liquid supplying unit to the liquid chamber,
   wherein the controller varies the voltage waveform of the drive voltage on the basis of the phase signal.

2. The liquid injection device according to claim 1,
   wherein the controller varies the voltage waveform of the drive voltage by multiplying the voltage waveform by a compensation coefficient.

3. The liquid injection device according to claim 2,
   wherein the compensation coefficient is set according to a time elapsed from a time point of reception of the phase signal.

4. The liquid injection device according to claim 1,
   wherein the liquid supplying unit includes a piston pump configured to supply the liquid by moving a piston, and outputs the phase signal when the piston passes through a predetermined position.

5. The liquid injection device according to claim 1,
   wherein the voltage waveform includes a first portion in which the voltage is increased and a second portion in which the voltage is decreased,
   wherein the controller varies a time required for outputting the first portion when the controller varies the voltage waveform.

6. The liquid injection device according to claim 5, wherein the controller decreases the time when the pressure of the liquid supplied from the liquid supplying unit is increased.

\* \* \* \* \*